United States Patent [19]

Gabus

[11] 4,117,863
[45] Oct. 3, 1978

[54] CONTROL DEVICE FOR OPERATION BY THE MOUTH OF A HANDICAPPED PERSON

[75] Inventor: Jean-Claude Gabus, Hauterive, Switzerland

[73] Assignee: Carba S.A., Berne, Switzerland

[21] Appl. No.: 774,498

[22] Filed: Mar. 4, 1977

[30] Foreign Application Priority Data

Mar. 26, 1976 [CH] Switzerland .................. 3804/76

[51] Int. Cl.$^2$ .................. B60K 26/00; F16K 31/04
[52] U.S. Cl. .................. 137/601; 3/1.2;
128/1 R; 180/99; 200/81 R; 251/4
[58] Field of Search .................. 116/65, 137 R; 46/178,
46/179; 3/1.1, 1.2; 128/222; 251/4, 7; 138/122,
40; 180/99; 137/601

[56] References Cited

U.S. PATENT DOCUMENTS

| 1,682,341 | 8/1928 | Keplinger | 46/178 |
| 2,588,038 | 3/1952 | Pagenhardt | 46/178 X |
| 2,626,585 | 1/1953 | Mendes | 116/137 X |
| 2,885,686 | 5/1959 | Giamo | 3/1.1 |
| 2,912,821 | 11/1959 | Horak | 138/40 X |
| 3,103,911 | 9/1963 | Tappan et al. | 116/137 R |
| 3,315,703 | 4/1967 | Matthews et al. | 138/111 |
| 3,974,858 | 8/1976 | Nielson | 251/7 X |

Primary Examiner—Daniel M. Yasich
Attorney, Agent, or Firm—Young & Thompson

[57] ABSTRACT

The invention relates to detecting or control devices for the control of utilization circuits particularly by handicapped persons who can move only their jaws. By squeezing action of the mouth, signal lines in a pressurized fluid deformable control member are selectively controlled to perform needed control functions.

This device comprises a control member of a resiliently deformable material which comprises a central reinforced, non squeezable, passage and non reinforced radial passages.

The central passage and the radial passages are connected together at one end of the control member. At the other end of the control member the central passage is connected to a supply unit and the radial passages to a measuring unit by means of flexible tubular connections. A continuous signal is fed in the central passage and the intensity of the return signals in the radial passages depends on the mechanical deformation of the control member.

4 Claims, 2 Drawing Figures

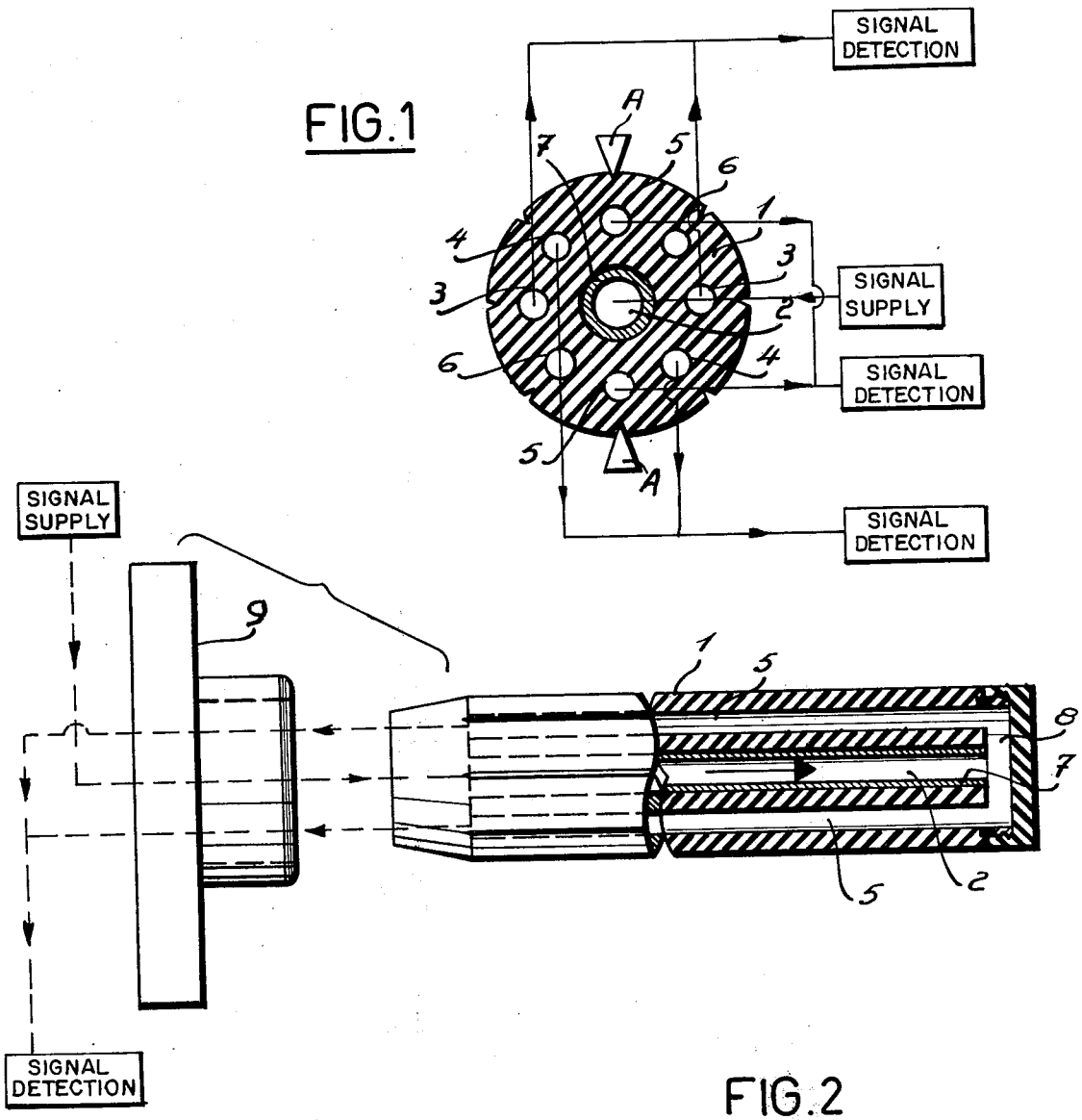

CONTROL DEVICE FOR OPERATION BY THE MOUTH OF A HANDICAPPED PERSON

The present invention has for its object a control device particularly intended to be used by invalids or handicapped persons who may for example use only their mouth. This control device permits to deliver different signals, and thus controls movements through known means.

This control device distinguishes itself by the fact that it comprises a control member having, made of a compressible material, a central reinforced passage and radial non reinforced passages; and by the fact that all these passages communicate at one of their ends and that they may be connected through their other end to the rest of the control device.

The attached drawing shows schematically and by way of example one embodiment of the detection device.

FIG. 1 is a transverse cross-section of the detecting member.

FIG. 2 is a longitudinal cross-section of the same.

The detecting device comprises supply and measuring means which will not be described here in detail and a control member intended to be connected to said supply and measuring means.

The control member comprises a mass of supple and resiliently deformable material in which a central passage 2 is provided as well as pairs of radial passages 3, 4, 5 and 6. The passages of a same pair of radial passages are symmetrically located with respect to the central passage 2. The central passage 2 is reinforced by means of a rigid tube 7 so as not to be deformed, even when the mass 1 is subjected to resilient deformations.

One end of this control member is provided with a chamber 8 connecting all the radial passages 3 to 6 and the central passage 2 together.

The other end of the control member is provided with means, (not shown) making it possible to connect individually each passage 2 to 6 to the supply and measuring means 9. Signal supply means can send a continuous signal in the central passage 2, for example a constant air or fluid flow, ultrasonic waves or sonic waves for example and measure the intensity of the return signals in each pair of radial passages 3 to 6.

The intensity of these return signals may be modified by squeezing the control member along one of its diameters, either with the fingers or with the teeth of the user. In fact, if one squeezes the mass 1 in the direction of the arrow A—A one reduces, due to a resilient deformation of the mass 1, the cross-section of the radial passages 5. Therefore the intensity of the return signals in this pair of passages 5 is reduced permitting to control a first operation, for example the starting of the driving motor of a roll-chair or of an electrical carriage.

By changing the location of the squeezing action, for example by rolling the control member between the upper and lower jaws one obtains a resilient deformation of the radial passages 4 or 6 according to the direction of displacement of the jaws. Therefore one obtains, by the reduction of the return signals of the pairs of passages 4 or 6 an indication relative to the direction which can be used to control a steering motor for an electrical carriage.

It is evident that according to the structure and the logic of the measuring means of the control device it is possible to control any kind of operations by means of the amplitude or intensity difference in the return signals coming from the radial passages.

The novel aspect of this apparatus resides in the control member which enables a handicapped person, which can use only his its jaws, nevertheless to control direction signals and for example to control the drive of an electrical rolling chair.

I claim:

1. A selective signalling device for manipulation by the mouth of a handicapped person, said device comprising an elongated member of resiliently deformable material having an elongated central passage which is non-deformable and at least one radially outer passage which is deformable under the selective squeezing pressure of the mouth of a user, said passages opening through said member at one end, the other end of said member being closed, the ends of said passages which are proximate to said closed end of said member communicating with each other at said closed end of said member, and means for delivering a continuous signal into said central passage from said one end of said member and for measuring the intensity of a return signal from said one end of said at least one radially outer passage, whereby selective deformation of said at least one radially outer passage under the pressure of the mouth of a user restricts said outer passage to change said return signal.

2. A member as claimed in claim 1, said at least one radially outer passage comprising a pair of said passages disposed in diametrically opposed relationship on opposite sides of said central passage.

3. A member as claimed in claim 2, there being at least three said pairs of radially outer diametrically opposed passages uniformly spaced about said member.

4. A member as claimed in claim 1, said central passage comprising a rigid tube inserted within said resiliently deformable material.

* * * * *